United States Patent [19]

Leroux et al.

[11] Patent Number: 5,773,698
[45] Date of Patent: Jun. 30, 1998

[54] CHIMERIC NITRILASE-ENCODING GENE FOR HERBICIDAL RESISTANCE

[75] Inventors: Bernard Leroux, Lozanne; Bernard Pelissier; Michel Lebrun, both of Lyons, all of France

[73] Assignee: Rhone-Poulenc Agrochimie, Lyons, France

[21] Appl. No.: 657,175

[22] Filed: Jun. 3, 1996

Related U.S. Application Data

[62] Division of Ser. No. 375,566, Jan. 13, 1995, Pat. No. 5,559,024, which is a continuation of Ser. No. 141,699, Oct. 26, 1993, abandoned, which is a continuation of Ser. No. 2,682, Jan. 8, 1993, abandoned, which is a continuation of Ser. No. 711,400, Jun. 6, 1991, abandoned, which is a continuation of Ser. No. 326,003, Mar. 20, 1989, abandoned.

[30] Foreign Application Priority Data

Mar. 23, 1988 [FR] France .................................. 88 04130

[51] Int. Cl.$^6$ ............................... A01H 5/00; C12N 5/04; C12N 15/31; C12N 15/82
[52] U.S. Cl. .............................. 800/205; 47/58; 435/419; 435/172.3; 536/23.2; 800/250
[58] Field of Search .............................. 435/172.3, 320.1, 435/419; 536/23.2, 23.7; 800/205, DIG. 43, DIG. 44, DIG. 26, DIG. 14, DIG. 23, DIG. 15, DIG. 46, DIG. 25, DIG. 9, 250; 47/58

[56] References Cited

U.S. PATENT DOCUMENTS 4,810,648  3/1989  Stalker ..................................... 435/191

FOREIGN PATENT DOCUMENTS

WO 87/04181  7/1987  WIPO .

*Primary Examiner*—David T. Fox
*Assistant Examiner*—Amy J. Nelson
*Attorney, Agent, or Firm*—Burns, Doane, Swecker & Mathis, L.L.P.

[57] ABSTRACT

Chimeric gene which is usable for endowing plants with resistance to a herbicide based on 3,5-dihalo-4-hydroxybenzonitrile, comprising at least one gene coding for resistance to this herbicide, a foreign promoter and, optionally, a polyadenylation signal region, wherein the promoter originates from a gene which is naturally expressed in plant cells and is chosen from the group comprising the promoter of the 35 S RNA for cauliflower mosaic virus (CaMV 35S) and the promoter of the small subunit (SSU) of sunflower (*Helianthus annuus*) ribulose-1,5-bisphosphate carboxylase/oxygenase (RubisCO).

5 Claims, 4 Drawing Sheets

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:1:

```
ACACGCTGAC AAGCTGACTC AGCTAGAGTC GAATTC                                    36
```

( 2 ) INFORMATION FOR SEQ ID NO:2:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:2:

```
ATTGGATTCT CGACCATCGA ATTC                                                 24
```

( 2 ) INFORMATION FOR SEQ ID NO:3:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:3:

```
GAATTCGAGC TCGGTACCCC ATGG                                                 24
```

( 2 ) INFORMATION FOR SEQ ID NO:4:

( i ) SEQUENCE CHARACTERISTICS:
        ( A ) LENGTH: 56 base pairs
        ( B ) TYPE: nucleic acid (C) STRANDEDNESS: single
(D) TOPOLOGY: linear (ii) MOLECULE TYPE: DNA (genomic)

(xi) SEQUENCE DESCRIPTION: SEQ ID NO:4:

GAATTCCCAG CAAGCAAGCA GCGAGTACAT ACATACTAGG CAGCCAGGCA GCCATG    56

(2) INFORMATION FOR SEQ ID NO:5:

(i) SEQUENCE CHARACTERISTICS:
        (A) LENGTH: 25 base pairs
        (B) TYPE: nucleic acid
        (C) STRANDEDNESS: single
        (D) TOPOLOGY: linear     (ii) MOLECULE TYPE: DNA (genomic)

(xi) SEQUENCE DESCRIPTION: SEQ ID NO:5:

GAATTCCGAA AGACAAAGAT TATCG    25

(2) INFORMATION FOR SEQ ID NO:6:

(i) SEQUENCE CHARACTERISTICS:
        (A) LENGTH: 23 base pairs
        (B) TYPE: nucleic acid
        (C) STRANDEDNESS: single
        (D) TOPOLOGY: linear     (ii) MOLECULE TYPE: DNA (genomic)

(xi) SEQUENCE DESCRIPTION: SEQ ID NO:6:

AAGCTTGCAT GCCCGATGGG CAG    23

(2) INFORMATION FOR SEQ ID NO:7:

(i) SEQUENCE CHARACTERISTICS:
        (A) LENGTH: 12 base pairs
        (B) TYPE: nucleic acid
        (C) STRANDEDNESS: single
        (D) TOPOLOGY: linear     (ii) MOLECULE TYPE: DNA (genomic)

(xi) SEQUENCE DESCRIPTION: SEQ ID NO:7:

CAATGCATGA AG    12

(2) INFORMATION FOR SEQ ID NO:8:

(i) SEQUENCE CHARACTERISTICS:
        (A) LENGTH: 25 base pairs
        (B) TYPE: nucleic acid
        (C) STRANDEDNESS: single
        (D) TOPOLOGY: linear     (ii) MOLECULE TYPE: DNA (genomic)

(xi) SEQUENCE DESCRIPTION: SEQ ID NO:8:

GTTCAATGCA TGCAGGTGTG GCCAC    25

(2) INFORMATION FOR SEQ ID NO:9:

(i) SEQUENCE CHARACTERISTICS:
        (A) LENGTH: 17 base pairs
        (B) TYPE: nucleic acid
        (C) STRANDEDNESS: single
        (D) TOPOLOGY: linear     (ii) MOLECULE TYPE: DNA (genomic)

( x i ) SEQUENCE DESCRIPTION: SEQ ID NO:9:

AAGAGTCTGT CCATCAC 17

( 2 ) INFORMATION FOR SEQ ID NO:10:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:10:

GTAAAACGAC GGCCAGT 17

( 2 ) INFORMATION FOR SEQ ID NO:11:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:11:

CAATGCATGC 10

CHIMERIC NITRILASE-ENCODING GENE FOR HERBICIDAL RESISTANCE

This application is a divisional of application Ser. No. 08/375,566, filed Jan. 13, 1995, now issued as U.S. Pat. No. 5,559,024, which is a continuation of Ser. No. 08/141,699, filed Oct. 26, 1993, now abandoned which is a continuation of Ser. No. 08/002,682, filed Jan. 8, 1993, now abandoned, which is a continuation of Ser. No. 07/711,400, filed Jun. 6, 1991, now abandoned, which is a continuation of Ser. No. 07/326,003, filed Mar. 20, 1989 now abandoned.

The present invention relates to a new chimeric gene which is usable for endowing plants with resistance to a herbicide based on 3,5-dihalo-4-hydroxybenzonitrile, to a process for transforming plant cells using this gene and to the transformed plants regenerated from these cells.

It is known, from European Application 229,042, to endow plants with resistance to a herbicide of the type mentioned above, in particular 3,5-dibromo-4-hydroxybenzonitrile or bromoxynil, by introducing into the genome of the plants a gene coding for a nitrilase specific for the degradation of these herbicides. While this technique gives useful results, it requires improvement in order to increase the chances of success and enhance its economic potential, especially regarding the level of expression in the plants and, accordingly, the quality of the resistance of the plants to these herbicides.

In the present description, "plant" means any differentiated multicellular organism capable of photosynthesis, and "plant cell" means any cell derived from a plant and capable of forming undifferentiated tissues such as calluses or embryos, or differentiated tissues such as parts of a plant or plants or seeds.

The object of the invention is to satisfy this need.

SUMMARY OF THE INVENTION

The present invention relates to a chimeric gene which is used for endowing plants with resistance to a herbicide based on a 3,5-dihalo-4-hydroxybenzonitrile, comprising at least one gene coding for a nitrilase for resistance to this herbicide, a foreign promoter and, optionally, a polyadenylation signal region, wherein the promoter originates from a gene which is naturally expressed in plant cells and is chosen from the group comprising the promoter of the 35 S RNA for cauliflower mosaic virus (CaMV 35S) and the promoter of the small subunit (SSU) of sunflower (*Helianthus annuus*) ribulose-1,5-bisphosphate carboxylase/oxygenase (RubisCO).

The promoter of the chimeric gene according to the invention originates from a gene which is naturally expressed in plants, i.e. of a non-plant type, e.g. a viral type such as the 35 S RNA of cauliflower mosaic virus (CaMV 35S), or alternatively and preferably a plant type from monocotyledonous or dicotyledonous plants, especially the small subunit of sunflower (*Helianthus annuus*) ribulose-1, 5-bisphosphate carboxylase/oxygenase (RubisCO). It is possible to use these promoters alone or in combination. The choice depends on the nature of the (mono- or dicotyledonous) plant to be transformed. Thus, it is preferable to use the sunflower small subunit RubisCO for the transformation of a dicotyledonous plant.

Each of these promoters may be obtained as follows:
1) Promoter of the 35 S RNA of cauliflower mosaic virus CaMV 35S):

The isolation of this promoter has been described by Odell et al. (1985). A clone (pJO5-2) containing approximately 850 bp upstream from the transcription initiation site was chosen for the constructions described herein. An EcoRI-HindIII fragment was isolated, the ends were made blunt with Klenow polymerase and the fragment was cloned into the vector pUC 19 (Yannish-Perron et al., 1985) at the HincII site. This clone was digested by the action of XbaI and PstI, and the fragment obtained was treated with phage T4 polymerase in order to make the ends blunt. This fragment was cloned into pUC19 Cm (Buckley, 1985) cut with SmaI and XbaI, and treated with Klenow polymerase. The clone thereby obtained was designated pRPA-BL I45. By treatment of the 3' terminal AccI site with Klenow polymerase and by ligating it with the EcoRI site, treated with Klenow polymerase, of the fragments situated downstream from this promoter, an EcoRI site is re-formed and the sequence [SEQ ID NO.: 1] thereby obtained, starting from the transcription initiation site, is as follows:

A C A C G C T G A C A A G C T G A C T C A G C T A G
A G T C <u>G A A T T C</u>
    EcoRI 2) The promoter of the small subunit of sunflower (*Helianthus annuus*) ribulose-1,5-bisphosphate carboxylase/oxygenase (RubisCO):

The gene from which this promoter is derived has been isolated by Wacksman et al. (1987). An EcoRI fragment containing the promoter of this gene was cloned into mp 18, the 3' portion of the promoter directly upstream from the polylinker of this vector. This clone was then linearised with BstXI and treated with Bal31 exonuclease. The mixture of fragments thereby obtained was treated with SalI followed by Klenow polymerase, and finally ligated at low DNA concentration. The clones obtained following this manipulation were sequenced, and one of them possessing the following sequence downstream from the putative transcription initiation site was selected:

. . . 5' A T T G G A T T C 3' . . .

A ClaI linker (A T C G A T) was introduced at the PstI site of this clone. Thus, by treatment of this ClaI site with Klenow polymerase and ligation with the EcoRI site, treated with Klenow polymerase, of the fragments which are placed downstream from this promoter, an EcoRI site is re-formed and the sequence [SEQ ID NO.: 2] thereby obtained, starting from the putative transcription initiation site is as follows:

A T T G G A T T C T C G A C C A T C <u>G A A T T C</u>
             Eco RI According to another aspect of the invention, the chimeric gene comprises a non-translated intermediate region (linker) between the coding gene and the promoter, and which can be chosen from the group comprising:
on the one hand, the linker of pUC 19, modified by cloning and having the following sequence [SEQ ID NO.: 3]

<u>G A A T T C</u> G A G C T C G G T A C C <u>C C A T G G</u>
EcoRI             NcoI on the other hand, the non-translated region of the small subunit of maize RubisCO: this region is derived from the cDNA corresponding to the gene described by Lebrun et al. (1987). It is an EcoRI-NcoI fragment which has the following sequence [SEQ ID NO.: 4]

on the other hand, the non-translated region of the small subunit of sunflower RubisCO: this region is derived from the cDNA isolated by Waksman and Freyssinet (1987). It has not been isolated as such, and is always to be found preceding the transit peptide of sunflower RubisCO. The sequence [SEQ ID NO.: 5] is as follows:

The chimeric gene according to the invention optionally comprises a polyadenylation region or site, which can be, e.g.:

1) The polyadenylation site of the nopaline synthase gene of pTi 37 (Bevan et al., 1983). This site is contained in a 260-bp MboI fragment (Fraley et al., 1983, patent application PCT 84/02913) which has been treated with Klenow polymerase and cloned into the SmaI site of M13mp18 in order to introduce BamHI and EcoRI sites, respectively, at the 5' and 3' ends. The BamHI site was treated with *Vigna radiata* nuclease and cloned at the SalI site, treated with Klenow polymerase, of pUC 19. This fragment now contains at its 5' end a HindIII site, which can be ligated at the 3' end of the nitrilase gene.

2) The polyadenylation site of the gene of the small subunit of maize RubisCO: this site was isolated in the form of a 540-bp SmaI-BglII fragment of the gene described by Lebrun et al. (1987). A ClaI linker (ATCGAT) was introduced at the SmaI site. After cleavage with ClaI and filling-in with Klenow polymerase, this fragment was cloned into pUC19 cut with PstI and then treated with phage T4 polymerase and recut with BamHI. This manipulation enabled a HindIII site to be introduced at the 5' end of the polyadenylation site. The sequence [SEQ ID NO.: 6] obtained is as follows:

According to another aspect of the invention, the chimeric gene can optionally and preferably comprise, between the intermediate region and the nitrilase gene, a region coding for a transit peptide, chosen from the group comprising that of the small subunit of maize RubisCO and that of the sunflower small subunit. The function of the transit peptide in the natural gene is to permit the entry of the RubisCO small subunit into the stroma of the chloroplasts. They should likewise direct the nitrilase into this compartment in the case where they are introduced between the intermediate region described above and the structural gene for the nitrilase:

1) Transit peptide of the small subunit of maize RubisCO: this fragment is derived from the cDNA corresponding to the gene described by Lebrun et al. (1987). It is a 141-bp NcoI-SphI fragment, the NcoI site covering the translation initiation codon and the SphI site, the cleavage site of the transit peptide. By treating the SphI end of this fragment with phage T4 polymerase and by ligating it with the NcoI end, treated with Klenow polymerase, of the nitrilase gene, a sequence is re-formed permitting the production of an unmodified nitrilase in the stroma of the chloroplasts.

2) Transit peptide of the small subunit of sunflower RubisCO: this fragment is derived from the cDNA isolated by Waksman and Freyssinet (1987). This sequence does not originally possess an SphI site at the cleavage site of the transit peptide. The sequence [SEQ ID NO.: 7] in this area is as follows:

A C was substitued by directed mutagenesis for the A indicated by an asterisk, thereby creating an SphI site. To perform this manipulation, the method of Zoller and Smith (1984) was used. A 270-bp EcoRI-SalI fragment was cloned into M13mp19am4. This vector, derived from M13mp19, possesses an amber mutation in gene 4 at base 5327, and cannot multiply in strains not possessing a suppresser for a mutation of this type. After purification of the single-stranded form of this recombinant phage, three oligonucleotides were hybridized in a single stage. The sequence [SEQ ID NOS.: 8–10] of these phosphorylated oligonucleotides is as follows:

They make possible, respectively:

1: the mutation of the fragment at the cleavage site of the transit peptide,

2: the correction of the amber mutation,

3: the priming of sequences upstream from the mutagenesis fragment.

After the simultaneous action of Klenow polymerase in the presence of the four nucleotides and phage T4 ligase, the mixture obtained was transformed into the strain HB2154 and then plated on a lawn of HB2151 (Carter et al., 1985). Among the clones obtained, those possessing an additional SphI site were sequenced in order to verify this structure, and one of them was used for the creation of chimeric genes. In the area of the cleavage site of the transit peptide, the sequence [SEQ ID NO.: 11] is now as follows:

This fragment is used in an identical manner to that used for the fragment coding for the transit peptide of the small subunit of maize RubisCO.

The assembling of the chimeric genes is performed according to the scheme in FIGS. 1 to 4 with the elements described above. The different genes thus created have been placed in one or two types of vectors and each assembly has been assigned a reference number. The different vectors thus produced are described in Table 1 below:

TABLE 1

Assembling of the different T DNAs containing chimeric genes for resistance to bromoxynil

| identification pRPA-BL | Vector | Promoter | | Linking region | | | Transient peptide | | | NOS polyA | Maize SSU polyA |
|---|---|---|---|---|---|---|---|---|---|---|---|
| | | CaMV 35S | Sunflower SSU | Maize 5' | Linker | Sunflower 5' | Maize | Sunflower | BR-XN | | |
| 203 | 150A 1 | + | | + | | | | | + | + | |
| 204 | 150A 1 | + | | + | | | + | | + | + | |
| 207 | 150A 1 | | + | + | | | | | + | + | |
| 208 | 150A 1 | | + | + | | | + | | + | + | |
| 217 | 150A 1 | + | | | + | | | | + | + | |
| 218 | 150A 1 | + | | | | + | | + | + | + | |
| 221 | 150A 1 | | + | | + | | | | + | + | |
| 222 | 150A 1 | | + | | | | | | + | + | |
| 235 | 142 | + | | + | | | | | + | + | |
| 236 | 142 | + | | | | + | | | + | + | |
| 237 | 142 | | + | + | | | | | + | + | |
| 238 | 142 | | + | | | + | | | + | + | |
| 249 | 142 | + | | + | | | | | + | | + |
| 250 | 142 | + | | | + | | | | + | | + |
| 251 | 142 | | + | + | | | | | + | | + |
| 252 | 142 | | + | | + | | | | + | | + |
| 447 | 142 | | + | | | + | | + | + | | + |

Vectors used:

The different chimeric constructions which led to the vectors pRPA-BL-142 and pRPA-BL-150Aalpha1 shown in FIGS. 1 to 4 were introduced into plants by means of the *Agrobacterium tumefaciens* transfer system. The transfer vectors constructed for this purpose have the following features:

an origin of replication and of transfer derived from pBR 322, a gene for bacterial selection, e.g. resistance to gentamicin, a COS site derived from phage lambda, both right and left borders of pTiA6 T DNA, optionally, an eucaryotic selection gene, with resistance to kanamycin, optionally, a fragment containing the lac alpha complementation gene of pUC18.

DETAILED DESCRIPTION OF THE INVENTION

Construction of pRPA-BL-142 (FIGS. 1 to 4)

Figure 1:
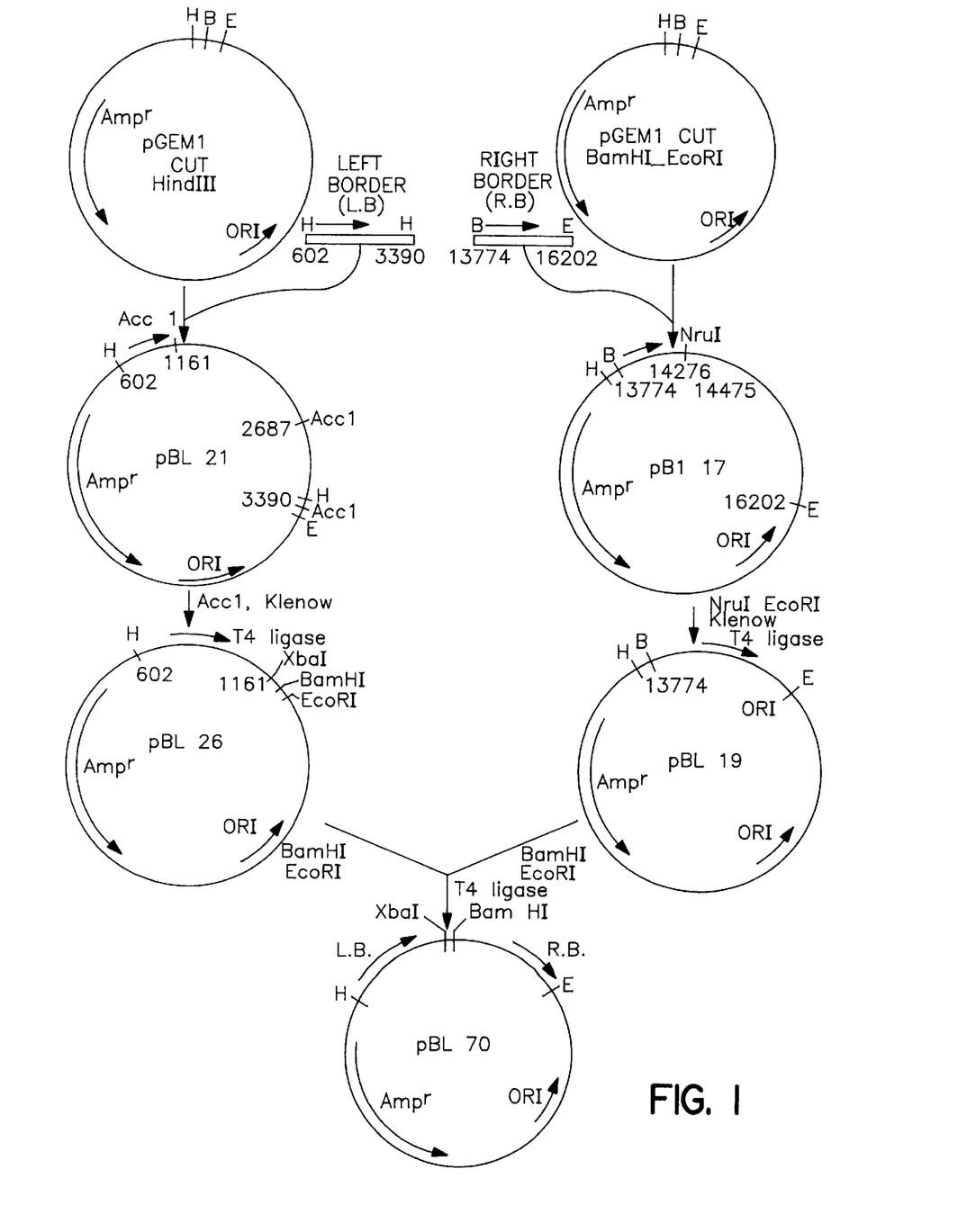
FIG. 1. Construction of pBL 70.

The right and left borders (FIG. 1) of the left-hand T DNA of pTiA6 were first subcloned:

right border:

a BamHI-EcoRI fragment extending from 13774 to 16202 in the numbering system of Barker et al (1983) was cloned into pGEM 1 (Promega Biotech) at the corresponding sites, giving pBL-17. This plasmid was digested with NruI (14276 and 14475) and with EcoRI (16202) and treated with Klenow polymerase. Ligation of the NruI site and the filled-in EcoRI site regenerates an EcoRI site at 14276 and gives plasmid pBL-19.

left border:

a HindIII fragment extending from 602 to 3390 in the system of Barker et al (1983) was cloned into the corresponding site of pGEM 1 giving pBL-21, in which the left border is on the opposite side from the polylinker. This plasmid was digested with Acc 1 (1161 and 2687) and treated with Klenow polymerase before being ligated. The resulting plasmid, pBL-26, contains a fragment extending from 602 to 1161 inserted between the HindIII and XbaI sites.

Creation of the T DNA:

By introducing the EcoRI-BamHI fragment of pBL-19 into the corresponding sites of pBL-26, a T DNA was re-formed possessing the right and left borders of pTiA6 in their natural orientation. The plasmid obtained is designated pBL-70.

Figure 2:
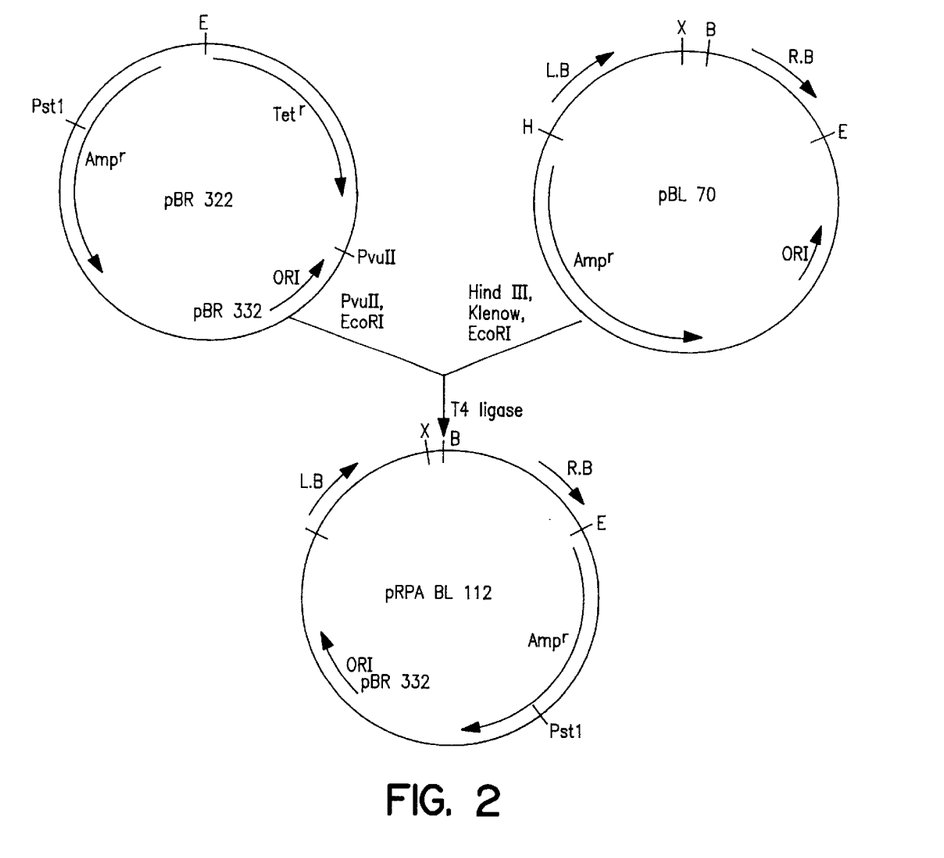
FIG. 2. Construction of pRPA BL 112.

Introduction of the T DNA into pBR 322 (FIG. 2):

After pBL-70 was cut with HindIII, this site was treated with Klenow polymerase and the plasmid recut with EcoRI. The fragment obtained was cloned into pBR 322 cut with PruII-EcoRI. The resulting clone is designated pRPA-BL-112.

Figure 3:
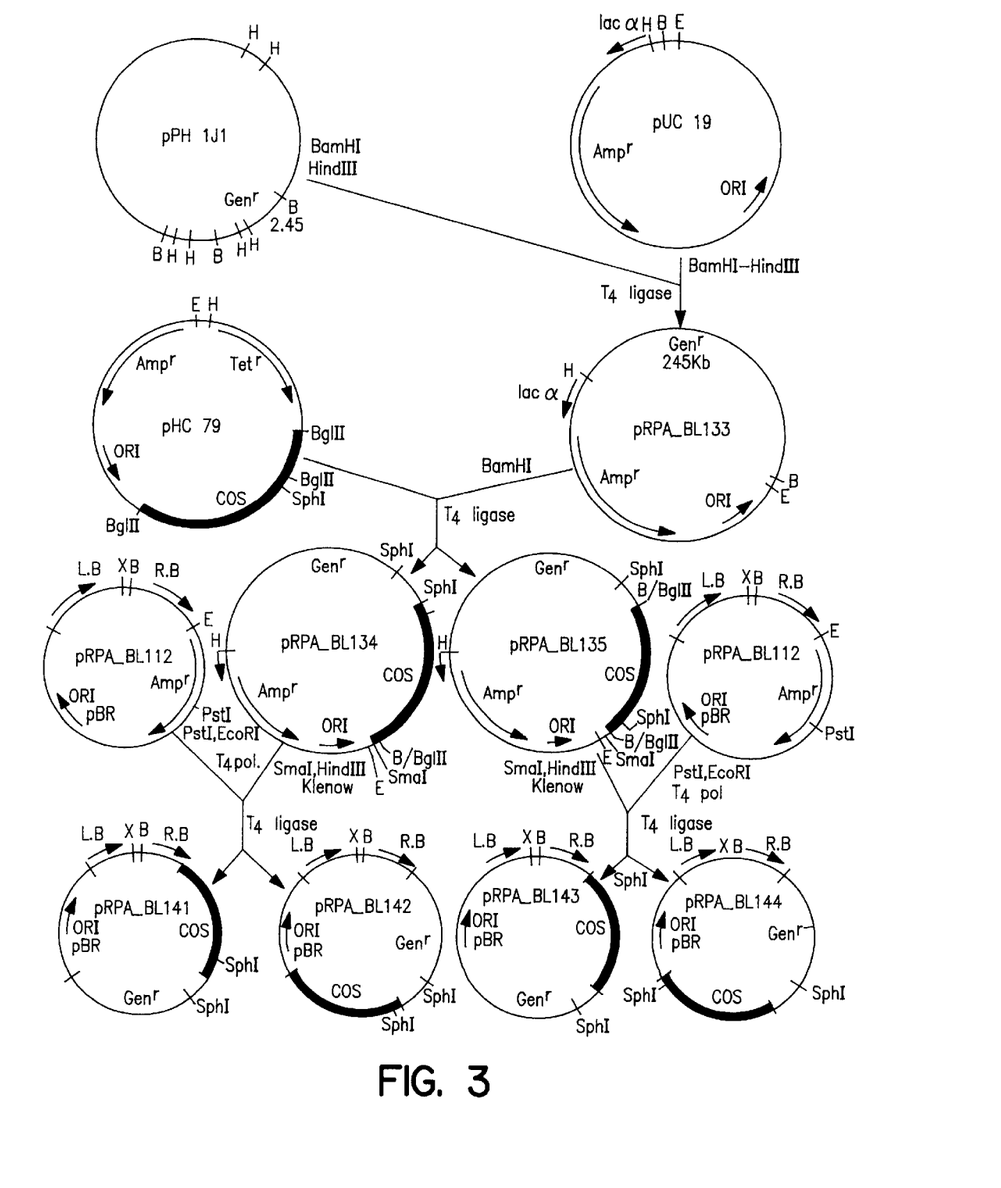
FIG. 3. Construction of pRPA__BL141, pRPA__BL142, pRPA__BL143, and pRPA__BL 144.
Figure 4:
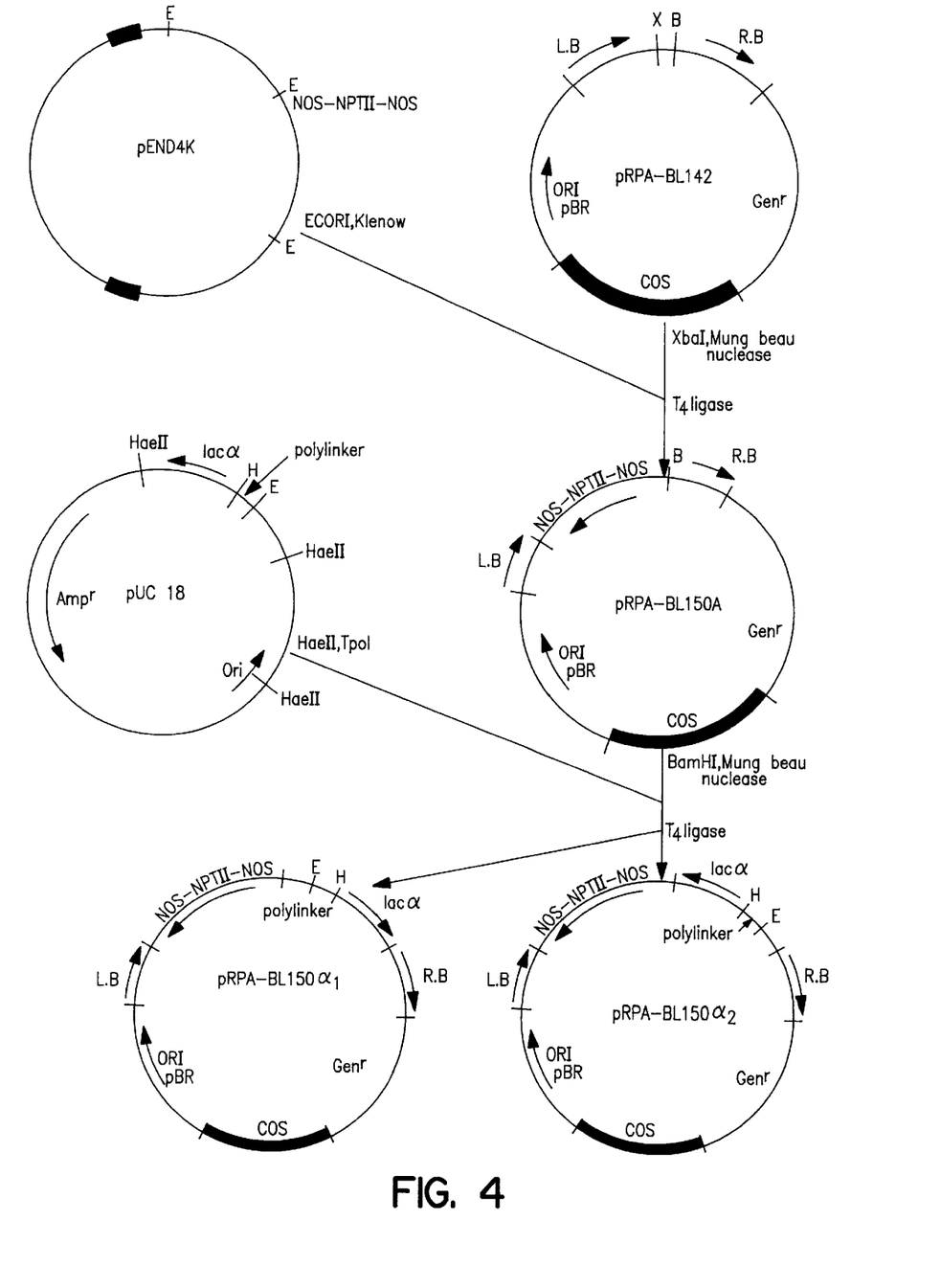
FIG. 4. Construction of pRPA-BL 150A 1.

Cloning of a gene for resistance to gentamicin (FIG. 3):

The gene for resistance to gentamicin was obtained from pPH1 J1I(Hirsh and Bringer, 1984). This plasmid was digested with BamHI and HindIII and the collection of fragments cloned into pUC 19 cut with the same enzymes. After selection on ampicillin+gentamycin, several clones containing a 2.45-kbp fragment were isolated. The clone selected for the subsequent manipulations was named pRPA-BL-133. At the BamHI site of this clone, a 1.6-kb BglII fragment, isolated from pHC 79 (Hohn and Collins, 1980) and containing the COS site of phage lambda, was introduced. This fragment, inserted in both orientations, enabled two clones pRPA-BL-134 and pRPA-BL-135 to be obtained.

Production of an integrative vector (FIG. 3):

In order to combine the different portions described above in one and the same vector, plasmids pRPA-BL-134 and pRPA-BL-135 were digested with SmaI and HindIII, and the insert containing the gene for resistance to gentamicin and the COS site of phage lambda was treated with Klenow polymerase. Plasmid pRPA-BL-112 was digested with PstI and EcoRI and treated with phage T4 polymerase. Both fragments were ligated, and the clones containing simultaneously resistance to gentamicin, the COS site, the T DNA and the origin of replication pBR 322 were selected. Plasmid pRPA-BL-134 gave rise to pRPA-BL-141 and pRPA-BL-142, and pRPA-BL-135 gave rise to pRPA-BL-143 and pRPA-BL-144. pRPA-BL-142 was selected for the introduction of the chimeric genes to be transferred into plants. From this vector, a construction containing a marker gene NOS-NPTII-NOS (FIG. 4) was obtained. Plasmid pRPA-BL-142 was digested with XbaI, and the ends were reduced by the action of *Vigna radiata* nuclease. Separately, pEND4 K (Klee et al, 1985) was digested with EcoRI and treated with Klenow polymerase. A 1.6-kbp fragment was isolated containing the chimeric gene for resistance to kanamycin, and introduced into pRPA-BL-142. The outcome of one of these fusions was named pRPA-BL-150 A, and was chosen for subsequent manipulations. In order to facilitate cloning into this vector, a HacII fragment treated with phage T4 polymerase, and containing the lac alpha complementation gene isolated from pUC 18 (Yannish-Perron et al, 1985), was introduced at the BamHI site treated with *Vigna radiata* nuclease. The two vectors obtained were named pRPA-BL-150Aalpha1 and pRPA-BL-150Aalpha2. pRPA-BL-150Aalpha1 was the vector used as a basis for the introduction of genes into plants.

Use of pRPA-BL-142 and pRPA-BL-150Aalpha1

These vectors are not maintained by themselves in Agrobacterium. In order to be maintained, they have to be integrated by simple recombination in a plasmid resident in this bacterium. This can take place via one of the fragments such as the site present on cosmids such as pVK 102, or the like, or such as the fragment of pBR 322 for plasmids possessing such sequences. This is the case for the Ti plasmid of strain GV3850 (Zambryski et al 1983), which is also a host for pRPA-BL-142 and pRPA-BL-150Aalpha1. Using the origin of replication pBR 322, these plasmids are transferred into Agrobacterium via the three-part system described by Ditte et al (1980).

Transformation of plant material

In order to test the efficacy of these chimeric genes, the latter were transferred into material according to the procedures described below:

A - Transformation procedures

1. Tobacco

The vector is introduced into the non-oncogenic strain of Agrobacterium EHA 101 (Hood et al 1987) carrying cosmid pTVK 291 (Komari et al 1986). The transformation technique is based on the procedure of Horsh et al (1985). The procedure for regeneration of industrial tobacco PBD6 (source: SEITA, France) is described below.

Regeneration of tobacco PBD6 from leaf explants is carried out on Murashige and Skoog (MS) medium base comprising 30 g/l of sucrose. The leaf explants are taken from plants cultivated in the greenhouse or in vitro, and transformed according to the leaf disc technique (Science 1985, vol 227, p. 1229–1231) in 3 successive stages.

The first stage comprises the induction of shoots on an MS+30 g of sucrose comprising 0.05 mg of NAA and 2 mg/l of BAP for 15 days.

The second stage enables the shoots formed during the 1st stage to develop; it is carried out on MS+30 g/l sucrose and does not contains any hormone, for 10 days.

The third stage enables the shoots, removed individually, to take root. This rooting medium contains salts, vitamins and sugar, diluted two-fold. It contains no hormone. After 10 to 15 days, the implanted shoots are taken to soil.

Determination of the hormone balance

The optimal regeneration frequency was obtained by testing 25 hormone balances BAP 0.2-0.5-1-1.5-2 and NAA 0-0.5-0.05 observed for 1.5 and 2 mg/l of BAP and 0.05 and 0.1 mg/l of NAA. The mixture 0.05 NAA and 2 mg/l BAP is adopted.

2. Other dicotyledons

The dicotyledons shown in Table 2 were transformed using the oncogenic strain of Agrobacterium A281 carrying cosmid pTVK291 associcated with the corresponding vector using the plant material as indicated in Table 2.

B - Measurement of the resistance to bromoxynil

1. Tobacco

Resistance was measured in vitro by the growth of calluses in the presence of bromoxynil (20 mg/l) in the form of the octanoate, and in vivo by spraying the leaves with bromoxynil or ioxynil at doses representing 10 times the dose recommended for an open-field treatment. The results obtained are summarized in Table 1a.

2. Other dicotyledons

The resistance was measured in vitro by the growth of calluses in the presence of 10 mg of bromoxynil (in the form of the octanoate) per liter of medium. In all cases, the results are positive. (Table 2).

TABLE 1a

Resistance of transformed tobacco to bromoxynil

| Identification | Resistance of tobacco | |
|---|---|---|
| pRPA-BL | Callus | Plants |
| 203 | + | + |
| 204 | + | + |
| 207 | + | + |
| 208 | + | + |
| 217 | + | + |
| 218 | + | + |
| 221 | + | + |
| 222 | + | + |
| 235 | + | + |
| 236 | + | + |
| 237 | + | + |
| 238 | + | + |
| 249 | + | + |
| 250 | + | + |
| 251 | + | + |
| 252 | + | + |

TABLE 2

Resistance of various dicotyledons to bromoxynil

| Plants | Plant material | pRPA-BL | | |
|---|---|---|---|---|
| | | 203 | 235 | 249 |
| *Lycopersicon esculentum* | hypocotyl | + | + | + |
| *Solanum tuberosum* | tuber | + | + | + |
| *Glycine max* | hypocotyl | + | + | + |

TABLE 2-continued

Resistance of various dicotyledons to bromoxynil

| Plants | Plant material | pRPA-BL 203 | 235 | 249 |
|---|---|---|---|---|
| *Beta vulgaris* | root | + | + | + |
| *Helianthus annuus* | hypocotyl | + | + | + |
| *Pisum sativum* | internode | + | + | + |
| *Brassica campestris oleacera* | hypocotyl | + | + | + |
| *Daucus carota* | root | + | + | + |
| *Phaseolus vulgaris* | hypocotyl | + |   | + |

We claim:

1. A plant cell containing a chimeric gene which confers resistance to a herbicide based on 3,5-dihalo-4-hydroxybenzonitrile, comprising at least one gene encoding nitrilase derived from bacteria, operably linked to a foreign promoter and a polyadenylation signal region, wherein the promoter originates from a gene which is naturally expressed in plant cells and is selected from the group consisting of the promoter of the 35S RNA gene of cauliflower mosaic virus (CaMV 35S) the promoter of the small subunit (SSU) gene of sunflower (*Helianthus annuus*) ribulose-1,5-biphosphate carboxylase/oxygenase (RubisCO), and a combination of the promoter of the 35S RNA gene of cauliflower mosaic virus (CaMV 35S) and the promoter of the small subunit (SSU) gene of sunflower (*Helianthus annuus*) ribulose-1,5-biphosphate carboxylase/oxygenase (RubisCO).

2. A transformed plant or part thereof, which is obtained by regeneration of plant cells according to claim 1.

3. A transformed plant seed obtained from plants according to claim 2.

4. A process for the selective weed control of plants using a herbicide based on 3,5-dihalo-4-hydroxy-benzonitrile, comprising application of the herbicide to weeds and to transformed plants according to claim 2.

5. A selectable marker for identification of transformed plant cells calluses, parts of plants or plants, comprising a chimeric gene which confers resistance to a herbicide based on 3,5-dihalo-4-hydroxybenzonitrile, wherein said chimeric gene comprises at least one gene encoding nitrilase derived from bacteria, operably linked to a foreign promoter and a polyadenylation signal region, wherein the promoter originates from a gene which is naturally expressed in plant cells and is selected from the group consisting of the promoter of the 35S RNA gene of cauliflower mosaic virus (CaMV 35S), the promoter of the small subunit (SSU) gene of sunflower (*Helianthus annuus*) ribulose-1,5-biphosphate carboxylase/oxygenase (RubisCO), and a combination of the promoter of the 35S RNA gene of cauliflower mosaic virus (CaMV 35S) and the promoter of the small subunit (SSU) gene of sunflower (*Helianthus annuus*) ribulose-1,5-biphosphate carboxylase/oxygenase (RubisCO).

\* \* \* \* \*